United States Patent
Tsunoda et al.

(10) Patent No.: US 7,291,755 B2
(45) Date of Patent: Nov. 6, 2007

(54) PROCESS FOR PRODUCING ALCOHOL AND/OR KETONE

(75) Inventors: Takashi Tsunoda, Kurashiki (JP); Kenji Akagishi, Kurashiki (JP); Atusi Watanabe, Okayama (JP)

(73) Assignee: Asahi Kasei Chemicals Corporation, Tokyo (JP)

( * ) Notice: Subject to any disclaimer, the term of this patent is extended or adjusted under 35 U.S.C. 154(b) by 203 days.

(21) Appl. No.: 10/541,367

(22) PCT Filed: Dec. 25, 2003

(86) PCT No.: PCT/JP03/16722

§ 371 (c)(1),
(2), (4) Date: Jul. 5, 2005

(87) PCT Pub. No.: WO2004/060843

PCT Pub. Date: Jul. 22, 2004

(65) Prior Publication Data

US 2006/0173220 A1    Aug. 3, 2006

(30) Foreign Application Priority Data

Jan. 6, 2003    (JP) .............................. 2003-000110

(51) Int. Cl.
C07C 45/27    (2006.01)
C07C 27/10    (2006.01)

(52) U.S. Cl. .................... 568/398; 568/398.8; 568/910

(58) Field of Classification Search ................ 568/398, 568/398.8
See application file for complete search history.

(56) References Cited

U.S. PATENT DOCUMENTS 3,636,156 A * 1/1972 Ozaki et al. ................ 568/400
3,987,104 A   10/1976 Vanhauten
4,022,837 A   5/1977  Schneider
4,560,804 A * 12/1985 Yeh et al. ................... 568/408
4,737,482 A *  4/1988 Yeh et al. ................... 502/220

FOREIGN PATENT DOCUMENTS

| EP | 0 614 872 A1 | 9/1994 |
|---|---|---|
| GB | 1 240 858 | 7/1971 |
| GB | 1 324 717 | 7/1973 |
| JP | 47-8046 | 3/1972 |
| JP | 49-61112 | 6/1974 |
| JP | 49-72209 | 7/1974 |
| JP | 49-34652 | 9/1974 |
| JP | 59-163335 | 9/1984 |

OTHER PUBLICATIONS

Edited by Shokubai Gakkai; "Shokubai Koza Dai 5 Kan"; Kodansha Scientific, pp. 260-269, (1985).

* cited by examiner

Primary Examiner—Sikarl A. Witherspoon
(74) Attorney, Agent, or Firm—Finnegan, Henderson, Farabow, Garrett & Dunner, L.L.P.

(57) ABSTRACT

The present invention relates to a method for producing an alcohol and/or a ketone from a corresponding alkene(s) in a gas phase in the presence of water vapor by the use of an oxide catalyst. According to the present invention, there is provided a method for producing an alcohol and/or a ketone by bringing a starting material containing an alkene(s), as a gas phase into contact with an oxide catalyst in the presence of water vapor to carry out the reaction, wherein the oxide catalyst satisfies the following requirements: (a) it comprises an oxide(s) of molybdenum and/or tin, and (b) the amount of carbonaceous substances accumulated on the oxide catalyst is controlled to be within a range of 0.1 to 10% by mass, during the reaction.

14 Claims, 1 Drawing Sheet

FIG. 1

PROCESS FOR PRODUCING ALCOHOL AND/OR KETONE

TECHNICAL FIELD

The present invention relates to a process for producing an alcohol and/or a ketone from a corresponding alkene(s) in a gas phase in the presence of water vapor by the use of an oxide catalyst.

BACKGROUND ART

The production of an alcohol and/or a ketone from a corresponding alkene by a gas phase reaction in the presence of water vapor includes, for example, the production of acetone from propylene, the production of methyl ethyl ketone (MEK) from 1-butene or 2-butene, the production of cyclohexanone from cyclohexene and the production of tert-butanol from isobutene. All of these products are industrially very important chemical substances as chemical starting materials or solvents.

As prior art reactions as the above-mentioned reaction, there are mainly exemplified a Wacker type reaction using a noble metal catalyst such as a palladium compound, and a reaction using a compound oxide catalyst of metals other than noble metals, such as molybdenum, tungsten, tin, cobalt and the like.

As an example of process in which the former reaction, i.e., the Wacker type reaction is carried out, there is a process in which a carbonyl compound is produced in the presence of an olefin, oxygen and water vapor by the use of a catalyst obtained by supporting palladium and/or a palladium compound and copper chloride on a carrier such as silica, alumina or the like (see, for example, JP-A-49-72209). The working example of JP-A-49-72209 discloses the production of methyl ethyl ketone (MEK) from 1-butene by the use of a catalyst obtained by supporting palladium chloride and copper chloride on silica.

In addition, as an example of process not using a chloride as a catalyst, there is a process in which a catalyst obtained by supporting a palladium salt and a vanadyl salt on active carbon is used for producing acetaldehyde or a ketone by subjecting an olefin to vapor phase oxidation with oxygen or an oxygen-containing gas in the presence of water vapor (see, for example, JP-A-59-163335). The working example of JP-A-59-163335 discloses the production of acetone from propylene by the use of a catalyst obtained by supporting palladium sulfate and vanadyl sulfate on active carbon.

These catalysts, however, are obtained by the use of the very expensive noble metal. Moreover, as a result of repeat experiment by the present inventors, it was found that both of the catalysts were deteriorated in activity in a short time.

As an example of process in which the latter reaction using no noble metal catalyst is carried out, there is a process in which an olefin is reacted with oxygen in the presence of water vapor by the use of a catalyst comprising molybdenum oxide and close-grained tin oxide uniformly distributed on a carrier (see, for example, JP-B-47-8046). The working example of JP-B-47-8046 discloses the production of acetone from propylene by the use of a catalyst obtained by supporting tin dioxide and molybdenum trioxide on silica.

As an example of process using a similar catalyst, there is a process in which a mixture of an olefin and water vapor is subjected to reaction by the use of a catalyst obtained by supporting molybdenum oxide, tin oxide and a specific amount of an alkali metal and/or an alkaline earth metal on a carrier (see, for example, JP-A-49-61112). The working example of JP-A-49-61112 discloses the production of MEK from trans-butene by the use of a catalyst obtained by supporting tin dioxide, molybdenum trioxide and sodium on silica.

In addition, there is a process in which a similar catalyst is used and a gas as starting material for reaction comprising an olefin, water vapor and a small amount of oxygen and a gas containing a large amount of oxygen are alternately brought into contact with the catalyst (see, for example, JP-B-49-34652). The working example of JP-B-49-34652 discloses the production of MEK from n-butene by the use of a catalyst obtained by supporting tin dioxide and molybdenum trioxide on silica.

However, as a result of repeat experiment by the present inventors, all of these processes using a catalyst comprising metals other than noble metals were found to be disadvantageous in that the selectivity of a ketone as a desired product obtained from an alkene fed is lowered because a very large amount of carbonaceous substances are produced on the catalyst by the reaction.

DISCLOSURE OF THE INVENTION

The present invention is directed to provide a production process in which in a reaction for producing an alcohol and/or a ketone from a corresponding alkene(s) in a gas phase in the presence of water vapor by the use of an oxide catalyst, the selectivity of the desired product(s) (the alcohol and/or the ketone) is greatly improved by suppressing the production of carbonaceous substances which are accumulated on the catalyst during the reaction.

The present inventors earnestly investigated in order to solve the above problem, and consequently found that it is adequate to the above purpose to use a catalyst which is as follows: (a) it comprises an oxide(s) of molybdenum and/or tin and (b) the amount of carbonaceous substances accumulated on the catalyst is controlled to be within a specific range. On the basis of this finding, the present invention has been accomplished.

That is, the present invention relates to the production processes described below.

(1) A method for producing an alcohol and/or a ketone from at least one corresponding alkene by bringing a starting material containing the alkene(s), as a gas phase into contact with an oxide catalyst in the presence of water vapor to carry out the reaction, wherein
said oxide catalyst satisfies the following requirements:
(a) it comprises an oxide(s) of molybdenum and/or tin, and
(b) the amount of carbonaceous substances accumulated on said oxide catalyst is controlled to be within a range of 0.1 to 10% by mass, during said reaction.

(2) A method according to the above item (1), which comprises recovering the unreacted alkene(s) and the alcohol and/or ketone from a reaction mixture obtained by said reaction, and recycling the unreacted alkene(s) as a portion of the starting material.

(3) A method according to the above item (1) or (2), wherein in carrying out said reaction by a fluidized bed reaction system, a catalyst recycling system is adopted which comprises taking out the oxide catalyst used in the reaction from a reactor, regenerating said oxide catalyst in the presence of an oxygen-containing gas, and returning the regenerated oxide catalyst to the reactor.

(4) A method according to the above item (3), wherein the amount of carbonaceous substances accumulated on the oxide catalyst to be returned to the reactor is controlled to be within a range of 0.1 to 10% by mass.

(5) A method according to the above item (3) or (4), wherein the temperature at the regeneration of the oxide catalyst in the presence of the oxygen-containing gas is 270 to 550° C.
(6) A method according to any one of the above items (3) to (5), wherein the mass ratio of the amount of the oxide catalyst returned to the reactor to the amount of the alkene(s) fed to the reactor ranges from 0.5 to 100.
(7) A method according to any one of the above items (1) to (6), wherein the amount of carbonaceous substances accumulated on the oxide catalyst is controlled to be within a range of 0.3 to 5% by mass.
(8) A method according to any one of the above items (1) to (7), wherein the atomic ratio X of molybdenum to the sum of tin and molybdenum in the oxide catalyst {Mo/(Sn+Mo); wherein Mo is the number of atoms of molybdenum in said oxide catalyst, and Sn is the number of atoms of tin in said oxide catalyst} is in a range excluding 0.29 and 0.51.
(9) A method according to any one of the above items (1) to (7), wherein the atomic ratio X of molybdenum to the sum of tin and molybdenum in the oxide catalyst {Mo/(Sn+Mo); wherein Mo is the number of atoms of molybdenum in said oxide catalyst, and Sn is the number of atoms of tin in said oxide catalyst} is in a range of $0 \leq X < 0.50$ (excluding 0.29).
(10) A method according to any one of the above items (1) to (7), wherein the atomic ratio X of molybdenum to the sum of tin and molybdenum in the oxide catalyst {Mo/(Sn+Mo); wherein Mo is the number of atoms of molybdenum in said oxide catalyst, and Sn is the number of atoms of tin in said oxide catalyst} is in a range of $0.01 \leq X \leq 0.24$.
(11) A method according to any one of the above items (1) to (10), wherein the molar ratio of the amount of oxygen gas fed to the reactor to the amount of the alkene(s) fed to the reactor ranges from 0.0 to 0.5.
(12) A method according to any one of the above items (1) to (11), wherein the molar ratio of the amount of water vapor fed to the reactor to the amount of the alkene(s) fed to the reactor ranges from 0.05 to 10.0.
(13) A method according to any one of the above items (1) to (12), wherein the whole or a portion of recovered water after said reaction is reused in said reaction.
(14) A method according to any one of the above items (1) to (13), wherein the alkene(s) is 1-butene and/or 2-butene.
(15) A method according to the above item (14), wherein the starting material containing 1-butene and/or 2-butene as the alkene(s) contains at least one compound selected from the group consisting of isobutene, butadiene, tert-butyl alcohol and methyl tert-butyl ether.

BEST MODE FOR CARRYING OUT THE INVENTION

The present invention is explained below in detail.
The catalyst used in the process of the present invention is a catalyst containing an oxide(s) of molybdenum and/or tin.
Although such an oxide may be used alone, employment of both molybdenum oxide and tin oxide in the form of a mechanical mixture and/or a compound oxide is effective in improving the catalytic activity and the selectivity of the desired product(s) and hence is more preferable. In addition, oxides of other elements may be added for further improving the catalytic activity and the selectivity of the desired product(s). Elements of group 4, group 5, group 6, group 8, group 9, group 10, group 11, group 14 and group 15 of the periodic table are preferable. These elements are more preferably as follows: the elements of group 4 are titanium and zirconium, the elements of group 5 are vanadium and niobium, the elements of group 6 are tungsten and chromium, the element of group 8 is iron, the element of group 9 is cobalt, the element of group 10 is nickel, the element of group 11 is copper, the element of group 14 is lead, and the elements of group 15 are bismuth, antimony and phosphorus. The periodic table referred to here is the 18-group type periodic table described in Chemical Society of Japan, "Kagaku Binran Kisohen I Fourth Revised Eddition", Maruzen Co., Ltd. (1993), p. I-56. Besides the above-mentioned oxides, a slight amount of any of oxides of alkali metals (e.g. sodium, potassium and rubidium) and alkaline earth metals (e.g. magnesium, calcium and barium) may be added.

In addition, the oxides described above are preferably used after being supported on a suitable carrier. The carrier is preferably an inorganic oxide such as silica, silica-alumina, alumina, titania, silica-titania, zirconia, silica-zirconia or the like, in particular, silica. Furthermore, clay such as kaolin, talc or the like may be added for increasing the mechanical strength of the catalyst.

When the oxide catalyst contains oxides of molybdenum and tin, the atomic ratio X of molybdenum to the sum of tin and molybdenum. {Mo/(Sn+Mo); wherein Mo is the number of atoms of molybdenum in said oxide catalyst, and Sn is the number of atoms of tin in said oxide catalyst} is preferably in a range excluding 0.29 and 0.51, more preferably in a range of $0 \leq X < 0.50$ (excluding 0.29), further more preferably in a range of $0.01 \leq X \leq 0.24$, still more preferably in a range of $0.05 \leq X \leq 0.24$, especially preferably in a range of $0.08 \leq X \leq 0.15$. When X is less than 0.01, the catalytic activity tends to be low. When X is 0.29 or more, the selectivity tends to be lowered. In addition, when X is 0.51 or more, crystals of molybdenum precipitate outsides the catalyst during the calcination of the catalyst, so that the crystals tend to lower the fluidity of the catalyst when the catalyst is used in a reaction carried out by a fluidized bed system. A range preferable for both the fluidity of the catalyst and the selectivity of the desired substance(s) is $0.01 \leq X \leq 0.24$.

A process for preparing the oxide catalyst used in the present invention is described below in detail.

The preparation of the catalyst is composed mainly of 1) a step of preparing a starting solution for the catalyst, and 2) a step of drying the starting solution for the catalyst and a step of calcining a precursor of the catalyst.

1) The step of preparing a starting solution for the catalyst

The chemical form(s) of a starting material(s) for the formation of an oxide(s) as active species for the catalyst (the term "oxide" hereinafter also includes compound oxides) is not particularly limited. As the starting material(s), there are preferably used salts and compounds, which form the oxide at 200 to 1000° C. The salts and compounds include, for example, nitrates, sulfates, acetates, oxalates, ammonium salts, chlorides and hydroxides. In addition, commercial oxides may be used as they are.

Usually, one or more starting materials are thoroughly dissolved in water or a suitable solvent at 20 to 80° C. In this case, the solution may be controlled so as to be acidic or alkaline, in order to increase the solubility of the starting material(s). When the starting material(s) is difficultly soluble, hydrogen peroxide or the like is added in some cases.

Although the starting solution may be dried as it is, it is preferable to mix the solution thoroughly with powder, a solution, a sol, a gel or the like, which contains a carrier component, in order to support the oxide(s) on a suitable carrier as described above.

In this case, when a nitrate, sulfate, chloride or the like is used as the starting material for the oxide, such a compound is preferably converted to a hydroxide by the addition of aqueous ammonia because it gives a corrosive gas in the subsequent calcination step. In addition, the mixture obtained above may be adjusted to an acidic pH or an alkaline pH in order to adjust a viscosity or the like.

2) The step of drying the starting solution for the catalyst/the step of calcining a precursor of the catalyst.

These steps comprise removing the solvent from the above-mentioned starting solution for the catalyst (the term "starting solution for the catalyst" hereinafter also includes starting solutions for the catalyst which contain a carrier component) by drying to obtain a precursor of the catalyst, and then converting the precursor to the oxide catalyst by a treatment such as calcination.

A method for drying the starting solution for the catalyst is not particularly limited. As this method, there are exemplified a method of removing the solvent from the starting solution for the catalyst with an evaporator under reduced pressure at 50 to 90° C., and then drying the residue in a vacuum dryer at 50 to 150° C. for 1 to 48 hours; a method of spraying the starting solution for the catalyst on a hot plate heated at 150 to 300° C., through a nozzle to dry the solution; and a method of drying the starting solution for the catalyst in a spray dryer (a spray hot-air dryer). Industrially, the drying in a spray dryer is preferable. The spray dryer refers to a hot-air dryer composed of a drying chamber, a starting-solution spraying portion, a hot-air inhalation/evacuation portion and a dry-powder recovering portion. Preferable spray drying conditions are as follows: said starting solution for the catalyst is fed by the use of a pump and sprayed in the drying chamber with a rotary atomizer (a centrifugal atomizer), a pressure nozzle, a two-fluid nozzle (a gas atomizer) or the like. Droplets of said starting solution for the catalyst sprayed are brought into contact with hot air controlled so as to have an inlet temperature of 150 to 500° C., in a counter-current manner or a parallel-current manner to be freed from the solvent by evaporation, and the residue was recovered as dry powder.

A method for calcining the thus obtained dry precursor of the catalyst is not particularly limited. The precursor is preferably calcined in an electric furnace at 400 to 1000° C. for 0.5 to 48 hours while introducing an inert gas (e.g. nitrogen) and/or an oxygen-containing gas.

In addition, the precursor may be treated with water vapor at 150 to 500° C. for 0.5 to 48 hours before or after the calcination in order to disperse a catalytically active species on the catalyst.

The catalyst in the present invention is used in the reaction after being molded or shaped, for example, in a columnar, cylindrical or spherical form according to the system of the reaction by a known molding or shaping method such as tablet compression, extrusion molding, spray molding or the like. Either the catalyst precursor or its calcination product may be subjected to the molding or shaping.

When the reaction according to the present invention is carried out in a fluidized bed reaction system, it is especially preferable to adopt a method comprising drying a starting solution for the catalyst in a spray dryer, obtaining a molded or shaped catalyst precursor, and calcining the catalyst precursor at 500 to 800° C. for 1 to 24 hours while introducing an oxygen-containing gas.

Next, the carbonaceous substances accumulated on the oxide catalyst used in the present invention are described.

The catalyst used in the reaction carried out in the present invention is such that the amount of carbonaceous substances accumulated on the catalyst (defined hereinafter) is controlled to be within a range of 0.1 to 10% by mass during the reaction.

Here, the carbonaceous substances refer to heavy substances which are composed mainly of carbon, are accumulated on the catalyst by a chemical reaction taking place through an organic compound, and are accumulated on the catalyst during the reaction without being scattered from the catalyst. Examples thereof are heavy substances accumulated on the catalyst in the production of an alcohol and/or a ketone from a corresponding alkene(s) or by their contact with a highly reactive organic compound which takes place separately from the above-mentioned reaction.

In the present invention, the amount of carbonaceous substances accumulated on the catalyst should be controlled to be within a range of 0.1 to 10% by mass as described above, and is preferably 0.3 to 8% by mass, more preferably 0.3 to 5% by mass, still more preferably 0.5 to 5% by mass, especially preferably 1 to 5% by mass. When the amount of carbonaceous substances accumulated is less than 0.1% by mass, the inhibitory effect on the production of carbonaceous substances by the reaction described hereinafter tends to be insufficient. When the amount is more than 10% by mass, the catalytic activity tends to be insufficient.

The amount of carbonaceous substances accumulated on the catalyst is defined by the following equation by measuring the mass of carbon of the catalyst having the carbonaceous substances accumulated thereon, with a CHN corder used for organic elemental analysis:

The amount of carbonaceous substances accumulated on the catalyst (% by mass)=$B/(A-B) \times 100$ A: the mass of the whole catalyst having the carbonaceous substances accumulated thereon (Kg), B: the mass of carbon of the catalyst having the carbonaceous substance accumulated thereon which is measured with the CHN corder (Kg).

Conditions of the analysis with the CHN corder may be general conditions of measurement with the CHN corder. Specifically, several milligrams to ten odd milligrams (increased or decreased depending on the amount of carbonaceous substances accumulated on the catalyst) of a sample is placed in a combustion furnace at 850° C. to burn organic components in the sample in a helium stream containing a definite amount of oxygen gas, and the mass of carbon is measured using the combustion gas.

As to a method for controlling the amount of carbonaceous substances accumulated on the catalyst, the amount can be controlled to be within the above-mentioned range, for example, by choosing suitable reaction conditions represented by the reaction conditions described in the present specification. In addition, for example, by choosing suitable regeneration conditions represented by the regeneration conditions described in the present specification, in regenerating the catalyst after the reaction having carbonaceous substances accumulated thereon, the amount of the carbonaceous substances accumulated on the regenerated catalyst to be reused in the reaction is controlled and as a result, the amount of the carbonaceous substances accumulated on the catalyst in a reactor can be controlled to be within the above-mentioned range.

Particularly when the reaction for producing an alcohol and/or a ketone from a corresponding alkene(s) is carried out by a system in which the catalyst is circulated between a fluidized bed reactor and a regenerator, the amount of carbonaceous substances accumulated on the catalyst to be returned to the reactor from the regenerator is preferably controlled to be within the above-mentioned range under the following regeneration conditions. That is, the catalyst is kept in an oxygen-gas-containing atmosphere having an oxygen gas concentration of 10 ppm by volume to 21% by volume, at 100 to 550° C. for 10 seconds to 10 Hr. The temperature is more preferably 270 to 550° C., in particular, 270 to 500° C. When the temperature is lower than 270° C., the restoration of the catalytic activity tends to be insufficient if severe reaction conditions are employed. When the temperature is higher than 550° C., the carbonaceous substances on the catalyst tend to be completely burnt (namely, their amount is below the lower limit of the range specified in the present invention).

When the reaction for producing an alcohol and/or a ketone from a corresponding alkene(s) is carried out in the absence of molecular oxygen or in the presence of a very small amount of molecular oxygen, the lattice oxygen of the oxide catalyst is used as an oxygen source at the time of the reaction. In such a case, the lattice oxygen can be advantageously replenished simultaneously with the regeneration, by treating the catalyst under the regeneration conditions described above.

In addition, the amount of carbonaceous substances accumulated on the catalyst can be controlled also by bringing the catalyst into contact with a highly reactive organic compound such as an aromatic hydrocarbon or a diene under suitable treating conditions (for example, the treatment is preferably carried out at 130 to 500° C. in an atmosphere of gas of the above-mentioned compound).

In any case, it is important that the amount of carbonaceous substances accumulated on the catalyst should be controlled to be within a range of 0.1 to 10% by mass during the reaction by properly choosing the reaction conditions, regeneration conditions, treatment conditions and the like.

Next, effects are described below which can be obtained when the amount of carbonaceous substances accumulated on the catalyst is controlled to be within a specific range.

Let us suppose the case where a fresh catalyst or a catalyst having almost no carbonaceous substance accumulated thereon (i.e. a catalyst on which the amount of carbonaceous substances accumulated thereon is below the lower limit of the range specified in the present invention) is used in the reaction for producing an alcohol and/or a ketone from a corresponding alkene(s). In this case, the amount of carbonaceous substances produced by the reaction and accumulated on the catalyst is very large, so that the yield of the desired product(s) from the alkene(s) fed (i.e. the selectivity of the desired product(s) among the products) is remarkably decreased.

On the other hand, in the case of the catalyst used in the present invention on which the amount of carbonaceous substances accumulated thereon is controlled to be within a specific range, the accumulation on the catalyst of the carbonaceous substances produced by the reaction can be markedly suppressed and as a result, the selectivity of the desired product(s) can be greatly improved. Furthermore, the catalyst used in the present invention makes it possible to increase the productivity for the desired product(s) to that attained by the use of a fresh catalyst.

Particularly when the above-mentioned reaction is continuously carried out in the absence of molecular oxygen or in the presence of a very small amount of molecular oxygen, the catalyst should be frequently regenerated in an oxygen-gas-containing atmosphere in order to retain the catalytic activity. This is because the lattice oxygen of the oxide catalyst used as an oxygen source for the reaction should be replenished. When in the regeneration, the carbonaceous substances accumulated on the catalyst are nearly perfectly removed as before for restoring the catalytic activity, the production of carbonaceous substances by the reaction and their excessive accumulation on the catalyst are caused again. As a result, loss of the starting material caused by its conversion to unnecessary carbonaceous substances is increased in proportion to the frequency of regeneration of the catalyst and moreover, the utility cost is increased. The catalyst used in the present invention permits remarkable suppression of the losses described above.

The process of the present invention is described below in detail.

The process of the present invention is a process for producing an alcohol and/or a ketone from a corresponding alkene(s) by bringing a starting material containing the alkene(s), as a gas phase into contact with an oxide catalyst in the presence of water vapor to carry out the reaction.

Although the mechanism of the reaction is not clear, the present inventors conjecture as follows: at first, the alcohol is produced by the hydration reaction of the alkene(s) with water vapor, and then the alcohol produced and molecular oxygen in the gas phase or oxygen in the solid phase (i.e. the lattice oxygen of the oxide catalyst) undergo oxidative dehydrogenation reaction to produce the ketone.

Preferable examples of the alkene(s) contained in the starting material for the reaction are propylene, 1-butene, 2-butene (cis and/or trans), pentene, hexene, cyclohexene, heptene, octene and cyclooctene. More preferable examples of the alkene(s) are propylene, 1-butene, 2-butene (cis and/or trans) and cyclohexene. Especially preferable examples of the alkene(s) are 1-butene and 2-butene (cis and/or trans). These may be used singly or as a mixture thereof. In particular, industrially, $C_4$ raffinate-1 obtained by removing butadiene (1,2-butadiene and/or 1,3-butadiene) from $C_4$ distillate obtained by thermal cracking of naphtha, by extraction, and $C_4$ raffinate-2 obtained by reacting $C_4$ raffinate-1 with $H_2O$ or methanol to remove isobutene contained therein, by its conversion to tert-butyl alcohol or methyl tert-butyl ether are useful starting materials. However, since isobutene, butadiene, tert-butyl alcohol and methyl tert-butyl ether cannot be completely removed, they may be contained in an amount of 1 mol or less, preferably 0.5 mol or less, more preferably 0.1 mol or less, especially preferably 0.05 mol or less, per mol of 1-butene and/or 2-butene. This is a beneficial characteristic which permits reduction of the purification cost of the starting material.

In addition, any of gases inert to the reaction, such as nitrogen gas, argon gas, carbon dioxide gas, methane gas, ethane gas, propane gas, butane gas and the like may be mixed with or allowed to accompany the starting material for the reaction as a diluent gas or a carrier gas.

The molar ratio of the amount of water vapor fed to a reactor to the amount of alkene(s) fed to the reactor is preferably in a range of 0.05 to 10.0, more preferably in a range of 0.2 to 5.0, especially preferably in a range of 0.5 to 2.0. When the molar ratio is less than 0.05, the reaction rate tends to be decreased. When the molar ratio is more than 0.05, the reaction rate tends to be increased. Even when the molar ratio is adjusted to more than 10.0, the effect of this increase is especially small and surplus energy for producing water vapor becomes necessary.

The above-mentioned reaction may be carried out in either the presence or the absence of molecular oxygen. As described above, the present inventors conjecture that when no molecular oxygen is present in the gas phase, the lattice oxygen of the oxide catalyst is used as an oxygen source for the reaction.

The molar ratio of the amount of oxygen gas fed to the reactor to the amount of the alkene(s) fed to the reactor is preferably in a range of 0.0 to 5.0, more preferably in a range of 0.0 to 1.0, still more preferably in a range of 0.0 to 0.5, especially preferably in a range of 0.0 to 0.3. When the amount of oxygen is excessive, the selectivity of the desired product(s) among the products tends to be lowered. The molar ratio is 0.0 when no molecular oxygen is present and the lattice oxygen of the oxide catalyst is used in the reaction. In the reaction according to the present invention, the above case where no molecular oxygen is present is most preferable.

The amount of the alkene(s) fed to the catalyst (weight hourly space velocity (WHSV)) is not particularly limited. The amount is preferably 0.01 to 10 $Hr^{-1}$, more preferably 0.05 to 5 $Hr^{-1}$, especially preferably 0.1 to $2Hr^{-1}$.

The weight hourly space velocity (WHSV) is defined by the following equation:

WHSV ($Hr^{-1}$)=the feed rate of the alkene(s) (Kg/Hr)/the amount of the catalyst (Kg)

The preferable range of the reaction temperature varies depending on the starting material. Typically, the reaction temperature is preferably 130 to 500° C., more preferably 200 to 450° C., especially preferably 230 to 350° C. The reaction pressure is not particularly limited. It is preferably 0.01 to 1 MPa, more preferably 0.03 to 0.5 MPa, especially preferably 0.05 to 0.3 MPa.

As a reaction system adopted in the process of the present invention, there are exemplified a fixed bed reaction system, a moving bed reaction system and a fluidized bed reaction system. However, since the reaction according to the present invention is often an exothermic reaction, the fluidized bed reaction system is preferable which permits easy control of the reaction temperature. An especially preferable reaction system is such that a fluidized bed reaction is carried out by a so-called catalyst recycling system in which the following procedure is repeated: while carrying out the reaction by a fluidized bed reaction system, the catalyst used in the reaction is continuously or intermittently taken out to a regenerator and is regenerated under the above-mentioned conditions to replenish the lattice oxygen of the catalyst to be returned to a reactor from the regenerator, and simultaneously with these operations, the amount of carbonaceous substances accumulated on the catalyst is controlled to be within a range of 0.1 to 10% by mass and the whole or a portion of the catalyst is continuously or intermittently returned to the fluidized bed reactor.

In this case, the mass ratio of the amount of the oxide catalyst returned to the reactor to the amount of the alkene(s) fed to the reactor is preferably 0.5 to 100, more preferably 2 to 100, especially preferably 10 to 100. When the mass ratio is less than 0.5, the steady activity of the catalyst tends to be low. When the mass ratio is 100 or more, insufficient enhancing effect on the steady activity of the catalyst tends to be obtained.

Sampling of the catalyst for measuring the amount of carbonaceous substances accumulated on the catalyst in the case of the above-mentioned reaction system is conducted as follows.

Since the catalyst is continuously or intermittently supplied to or discharged from the fluidized bed reactor or the catalyst regenerator, the amount of carbonaceous substances accumulated on the catalyst is likely to be locally distributed though the catalyst inside the reactor or regenerator is stirred by a flowing gas. In such a case, the amount of carbonaceous substances accumulated on the catalyst which is in the reactor or is returned to the reactor from the regenerator is defined by sampling the catalyst from a line for taking out the catalyst to the regenerator from the reactor or a line for returning the catalyst to the reactor from the regenerator, to obtain as homogeneous a sample as possible, and measuring the amount of carbonaceous substances accumulated on this catalyst sample. Specifically, the following is preferable: at least 1 g each of three or more samples of the catalyst are obtained, the amount of carbonaceous substances on each sample is measured, and the arithmetic mean of the measured values is calculated.

Figure 1:
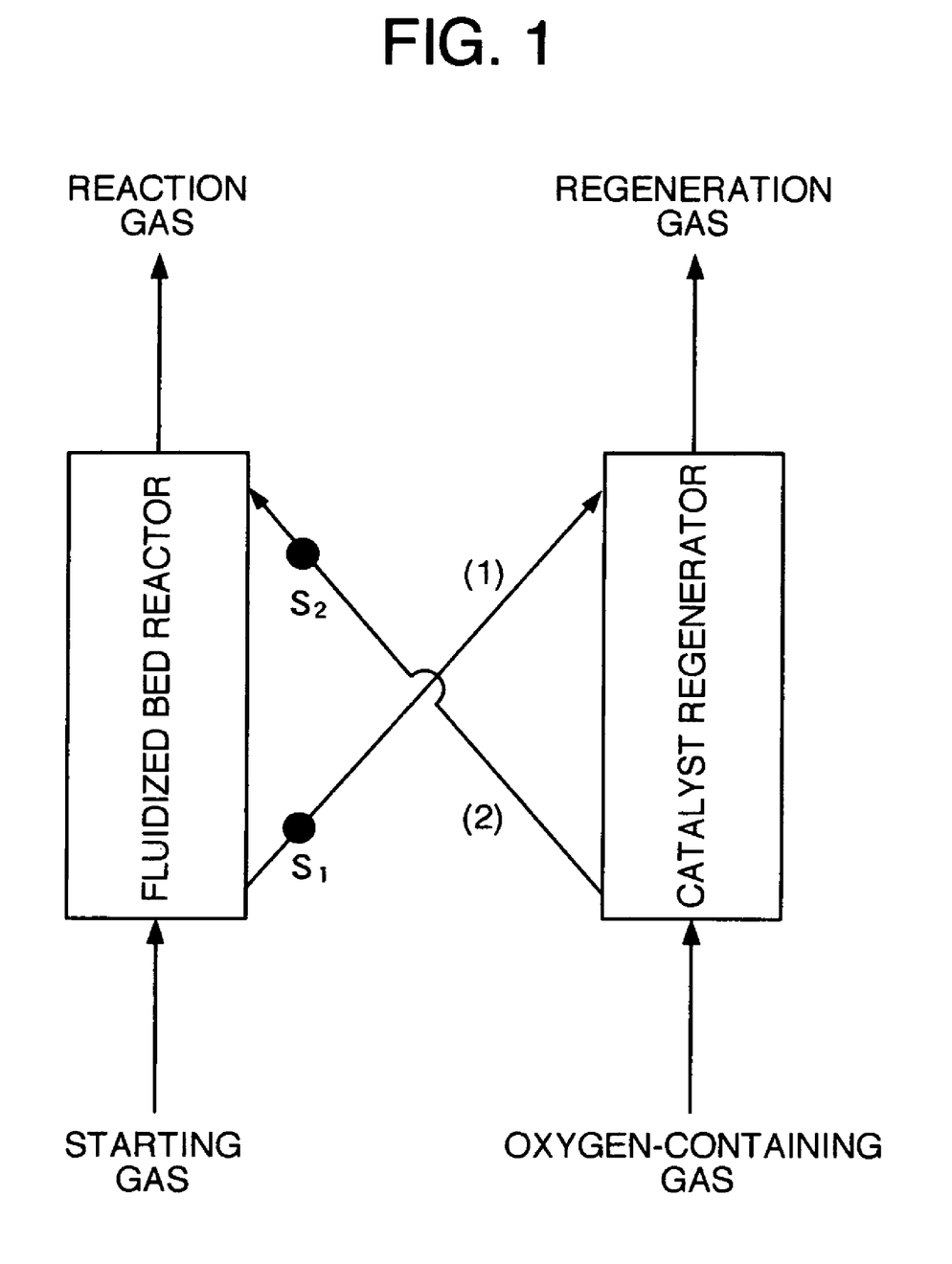

FIG. 1 shows a schematic view of the fluidized bed reactor and the catalyst regenerator. That is, in FIG. 1, the catalyst is sampled from $S_1$ on a catalyst taking-out line (1) and $S_2$ on a catalyst recycling line (2) and the amount of carbonaceous substances accumulated on the catalyst is measured.

In the present invention, since it is sufficient that the amount of carbonaceous substances accumulated on the catalyst in the reactor is controlled to be within a range of 0.1 to 10% by mass, preferably 0.3 to 5% by mass, it is sufficient that the amount of carbonaceous substances on each of the samples from $S_1$ and/or $S_2$ is within the above-mentioned range or that the mean of the amount values of carbonaceous substances on the samples from $S_1$ and $S_2$ is within this range.

From a reaction mixture containing an alcohol and/or a ketone which is obtained by the reaction described above, the alcohol and/or the ketone can be recovered by known recovery, separation and purification procedures such as cooling, distillation, extraction and the like. The unreacted alkene(s) is separated from the reaction mixture and then can, if necessary, be utilized as a portion of the starting material for the reaction by recycling.

Recovered water obtained by liquefaction by cooling of the whole or a portion of water vapor used in the reaction can be reused in the reaction even if it contains reaction by-products to a certain extent. For example, recovered water containing by-products such as acetone and acetic acid produced by the reaction of 1-butene can be reused in the reaction. This is a beneficial characteristic which permits marked reduction of a load of the disposal of a waste solution.

For example, when MEK is produced from 1-butene and/or 2-butene, the reaction mixture is cooled to condense MEK and water vapor. The cooled mixture was subjected to gas-liquid separation and then MEK is recovered from the condensate by distillation. The whole or a portion of recovered water containing by-products after the recovery of MEK is recycled to be fed to the reactor in the form of water vapor. As to the gas phase not condensed, MEK accompanying the gas phase is liquefied and recovered by compression and cooling, and the unreacted 1-butene and/or 2-butene are separated from light gases such as carbon dioxide and recycled to be fed to the reactor.

BRIEF DESCRIPTION OF THE DRAWINGS

FIG. 1 is a schematic view of a reactor and a regenerator in the case where the reaction according to the present invention is carried out as fluidized bed reaction by a catalyst recycling method. In FIG. 1, the symbol (1) indicates a catalyst taking-out line and the symbol (2) indicates a catalyst recycling line.

EXAMPLES

The present invention is more specifically illustrated with the following examples and comparative examples. The present invention is not limited by these examples.

Analyzers and analysis conditions employed are described below.

(Reaction Gas Analysis)
Gas chromatography: Shimadzu GC-17A (mfd. by Shimadzu Corp.)
Capillary column: SPB-1 (Φ0.25×60 m) (mfd. by SPELCO Inc.)
INJ temperature: 250° C. FID temperature: 250° C.
Column temperature: 40° C.×10 min, heated at a rate of 5° C./min and maintained at 200° C. for 8 min.

(Analysis for Carbon Dioxide and Carbon Monoxide in Reaction Gas)
Gas chromatography: Shimadzu GC-8A (mfd. by Shimadzu Corp.)
Packed columns: parallel columns, i.e., Porapac Q (Φ3×2 m) (Waters Co.) and MS-5A (Φ3×3 m) (mfd. by Shimadzu Corp.)
INJ temperature: 70° C. TCD temperature: 70° C.
Column temperature: maintained at 70° C.

(Measurement of the Amount of Carbonaceous Substances Accumulated on a Catalyst)
CHN corder analyzer: Model MT-5 (mfd. by Yanaco)

(Analysis of the Chemical Composition of a Catalyst)
Chemical composition analyzer: EMPA (Scanning Electron Microanalyzer), X-650 (mfd. by Hitachi Ltd.)

Reference Example 1

Preparation of Catalyst A

In 60 L of pure water was dissolved 9380 g of stannic chloride pentahydrate, followed by adding thereto 3040 g of silica fine powder (Aerosil 200V, a trade name, mfd. by Nippon Aerosil, Co., Ltd.), and 8% by mass aqueous ammonia was added thereto with stirring at 500 rpm until the pH became 5 to 7, to obtain a white precipitate of silica and tin hydroxide. The white precipitate was filtered and then thoroughly washed with pure water. To the cake thus obtained was added an aqueous solution obtained by dissolving 660 g of ammonium molybdate in 12.7 L of pure water, to obtain a homogeneous slurry, after which the pH of the slurry was adjusted to 2 to 4 with concentrated nitric acid. This slurry was spray-dried in a spray dryer to obtain globular molded product powder. The molded product powder obtained was calcined in an electric furnace at 650° C. for 1 hour in an air atmosphere. The composition of catalyst A thus obtained was analyzed with an EPMA composition analyzer and found to be as follows: $SnO_2$ 51% by mass, $MoO_3$ 7% by mass, and $SiO_2$ 42% by mass. The Mo/(Sn+Mo) atomic ratio of this catalyst A was 0.13, and catalyst A had a smoothly globular shape suitable for a fluidized bed catalyst and had a sufficient mechanical strength.

Reference Example 2

Preparation of Catalyst B

Catalyst B having a different composition was prepared by substantially the same process as in Reference Example 1. The composition of this catalyst B was as follows: $SnO_2$ 48% by mass, $MoO_3$ 11% by mass, and $SiO_2$ 41% by mass. The Mo/(Sn+Mo) atomic ratio of this catalyst B was 0.19, and catalyst B had a smoothly globular shape suitable for a fluidized bed catalyst and had a sufficient mechanical strength.

Reference Example 3

Preparation of Catalyst C

Catalyst C having a different composition was prepared by substantially the same process as in Reference Example 1. The composition of this catalyst C was as follows: SnO2 65% by mass, $MoO_3$ 5% by mass, and $SiO_2$ 30% by mass. The Mo/(Sn+Mo) atomic ratio of this catalyst C was 0.07, and catalyst C had a smoothly globular shape suitable for a fluidized bed catalyst and had a sufficient mechanical strength.

Reference Example 4

Preparation of Catalyst D

Catalyst D was prepared by substantially the same process as in Reference Example 1. The composition of this catalyst D was as follows: $SnO_2$ 31% by mass, $MoO_3$ 30% by mass, and $SiO_2$ 39% by mass. The Mo/(Sn+Mo) atomic ratio of this catalyst D was 0.50. In the case of catalyst D, molded product powder formed a mass and hence could not be uniformly calcined. Thus, catalyst D was unsuitable as a fluidized bed catalyst.

On the basis of these facts, it may safely be said that Mo/(Sn+Mo) is preferably less than 0.50, more preferably 0.24 or less.

Reference Example 5

Preparation of Catalyst E

Catalyst E comprising oxides of Cr and Mo was prepared by substantially the same process as in Reference Example 1 except for using chromium trichloride hexahydrate in place of stannic chloride pentahydrate. The composition of this catalyst E was as follows: $Cr_2O_3$ 42% by mass, $MoO_3$ 17% by mass, and $SiO_2$ 41% by mass. The Mo/(Cr+Mo) atomic ratio of this catalyst E was 0.18, and catalyst E had a smoothly globular shape suitable for a fluidized bed catalyst and had a sufficient mechanical strength.

Reference Example 6

Preparation of Catalyst F

Catalyst F comprising oxides of Ti and Mo was prepared by substantially the same process as in Reference Example 1 except for using titanium tetrachloride in place of stannic chloride pentahydrate. The composition of this catalyst F was as follows: $TiO_2$ 44% by mass, $MoO_3$ 17% by mass, and $SiO_2$ 39% by mass. The Mo/(Ti+Mo) atomic ratio of this catalyst F was 0.18, and catalyst F had a smoothly globular shape suitable for a fluidized bed catalyst and had a sufficient mechanical strength.

Reference Example 7

Preparation of Catalyst G

Catalyst G comprising only an oxide of Sn was prepared by substantially the same process as in Reference Example 1 except for omitting ammonium molybdate. The composition of this catalyst G was as follows: $SnO2$ 45% by mass and $SiO_2$ 55% by mass. This catalyst G had a smoothly globular shape suitable for a fluidized bed catalyst and had a sufficient mechanical strength.

Reference Example 8

Preparation of Catalyst H

Catalyst H was prepared by substantially the same process as in Reference Example 1 except for using alumina sol as a portion of a carrier. The composition of this catalyst H was as follows: $SnO_2$ 51% by mass, $MoO_3$ 7% by mass, $SiO_2$ 28% by mass, and $Al_2O_3$ 14% by mass. The Mo/(Sn+Mo) atomic ratio of this catalyst H was 0.13, and catalyst H had a smoothly globular shape suitable for a fluidized bed catalyst and had a mechanical strength higher than that attained by the use of a carrier composed of only silica.

Example 1

Catalyst A was packed into a reaction apparatus composed of a fluidized bed reactor and a catalyst regenerator and shown in FIG. 1, and fluidized bed reaction was carried out by a catalyst recycling system in which the reaction and the regeneration of the catalyst were continuously carried out while circulating catalyst A between the reactor and the regenerator. A starting material having a composition of 1-butene/water vapor/$N_2$=20/40/40 by volume was fed to the reactor at a weight hourly space velocity (WHSV)=0.2 relative to the amount of the catalyst in the reactor. The reaction temperature was 250° C. A mixed gas of air and $N_2$ was fed to the regenerator. The regeneration temperature was 320° C. The ratio of the amount of the catalyst recycled (i.e. the amount of the catalyst returned to the reactor from the regenerator) to the amount of 1-butene fed was 15 by mass, and the amount of carbonaceous substances accumulated on the catalyst to be returned to the reactor from the regenerator was 3.5% by mass. The above-mentioned reaction was continued for about 10 hours. A part of the reaction results obtained for 1 hour at any period during the reaction is shown in Table 1. The reaction results were substantially constant during the reaction.

Definitions are described below. All of them are based on the amount of carbon.
Amount of MEK produced (C mol): the amount of MEK produced for 1 hour
Selectivity of each component (mol%): P/(F-L)×100
  F: the amount of 1-butene and/or 2-butene fed (C mol)
  L: the amount of unreacted 1-butene and/or 2-butene (C mol)
  P: the amount of each component produced (C mol)
    2-Butene, a product of isomerization of 1-butene was considered as an unreacted material because it can be reused as a starting material.

The term "by-products" in the table means $CO_2$, CO, acetone, acetic acid, butyl alcohol, oligomers having 5 or more carbon atoms, and the like.

The term "selectivity of carbonaceous substances" in the table means the selectivity of carbonaceous substances freshly produced by the reaction.

Comparative Example 1

Fluidized bed reaction was carried out by the catalyst recycling system under substantially the same conditions as in Example 1 except for changing the regeneration temperature to 600° C. In this case, the amount of carbonaceous substances accumulated on the catalyst to be returned to the reactor from the regenerator was 0.03% by mass, namely, carbonaceous substances on the catalyst had been substantially completely removed. The above-mentioned reaction was continued for about 10 hours. A part of the reaction results obtained for 1 hour at any period during the reaction is shown in Table 1. The reaction results were substantially constant during the reaction.

From comparison of Example 1 with Comparative Example 1, it can be seen that when the amount of carbonaceous substances accumulated on the catalyst to be returned to the reactor from the regenerator was controlled to be within a range of 0.1 to 10% by mass, the selectivity of MEK was greatly improved in spite of the equal amount of MEK produced because the production of fresh carbonaceous substances was suppressed.

In addition, the results of Example 1 reveals that the value of the selectivity of MEK obtained in the case of excluding carbonaceous substances produced, which indicates the purity of MEK produced, is very high, namely, the separation and purification of MEK is easy.

Example 2

Fluidized bed reaction was carried out by the catalyst recycling system under substantially the same conditions as in Example 1 except for reducing the amount of air fed to the regenerator. In this case, the amount of carbonaceous substances accumulated on the catalyst to be returned to the reactor from the regenerator was 3.3% by mass. The above-mentioned reaction was continued for about 10 hours. A part of the reaction results obtained for 1 hour at any period during the reaction is shown in Table 1. The reaction results were substantially constant during the reaction.

Example 3

The Case Where Water Vapor/Alkene Ratio=1.0, and WHSV=0.4

Fluidized bed reaction was carried out by the catalyst recycling system under substantially the same conditions as in Example 1 except for feeding a starting material having a composition of 1-butene/water vapor/$N_2$=46/48/6 by volume, at a weight hourly space velocity (WHSV)=0.4 relative to the amount of the catalyst in the reactor. In this case, the amount of carbonaceous substances accumulated on the catalyst to be returned to the reactor from the regenerator was 3.1% by mass. The above-mentioned reaction was continued for about 10 hours. A part of the reaction results obtained for 1 hour at any period during the reaction is shown in Table 1. The reaction results were substantially constant during the reaction.

Example 4

The Case Where Catalyst B was used and the Ratio of the Amount of the Catalyst Recycled to the Amount of an Alkene was 60

Fluidized bed reaction was carried out by the catalyst recycling system under substantially the same conditions as in Example 1 except for using catalyst B, changing the regeneration temperature to 280° C. and changing the ratio of the amount of the catalyst recycled to the amount of 1-butene fed to 60 by mass. In this case, the amount of carbonaceous substances accumulated on the catalyst to be returned to the reactor from the regenerator was 3.7% by mass. The above-mentioned reaction was continued for about 10 hours. A part of the reaction results obtained for 1 hour at any period during the reaction is shown in Table 1. The reaction results were substantially constant during the reaction.

Example 5

The Case Where Catalyst B was used and the Amount of Carbonaceous Substances Accumulated was 0.5% by Mass Fluidized bed reaction was carried out by the catalyst recycling system under substantially the same conditions as in Example 1 except for using catalyst B, changing the regeneration temperature to 500° C. and feeding a starting material having a composition of 1-butene/water vapor/$N_2$=20/50/30 by volume, at a weight hourly space velocity (WHSV)=0.1 relative to the amount of the catalyst in the reactor. In this case, the amount of carbonaceous substances accumulated on the catalyst to be returned to the reactor from the regenerator was 0.5% by mass. The above-mentioned reaction was continued for about 10 hours. A part of the reaction results obtained for 1 hour at any period during the reaction is shown in Table 1. The reaction results were substantially constant during the reaction.

Example 6

The Case Where Catalyst C was used and $O_2$/Alkene Ratio=0.2

Fluidized bed reaction was carried out by the catalyst recycling system under substantially the same conditions as in Example 1 except for using catalyst C, feeding a starting material having a composition of 1-butene/water vapor/$N_2$/$O_2$=20/40/36/4 by volume to the reactor ($O_2$/1-butene=0.2), adjusting the ratio of the catalyst recycled to the amount of 1-butene fed to 0.5 by mass, and changing the regeneration temperature to 280° C. In this case, the amount of carbonaceous substances accumulated on the catalyst to be returned to the reactor from the regenerator was 2.5% by mass. The above-mentioned reaction was continued for about 10 hours. A part of the reaction results obtained for 1 hour at any period during the reaction is shown in Table 1. The reaction results were substantially constant during the reaction.

Example 7

The Case Where a Solution Recovered After the Reaction and Containing Reaction By-products was Reused Fluidized bed reaction was carried out by the catalyst recycling system under substantially the same conditions as in Example 1 except for using a residue obtained by separating MEK by distillation from the reaction solution described in Example 1, in place of water. This residue contained 4% by mass of acetic acid as by-product and 0.5% by mass of a high-boiling component. In this case, the amount of carbonaceous substances accumulated on the catalyst to be returned to the reactor from the regenerator was 3.5% by mass. The above-mentioned reaction was continued for about 10 hours. A part of the reaction results obtained for 1 hour at any period during the reaction is shown in Table 1. The reaction results were substantially constant during the reaction.

Example 8

The Case Where the Starting Alkene was Replaced with $C_4$ Raffinate-2

Fluidized bed reaction was carried out by the catalyst recycling system under substantially the same conditions as in Example 1 except for using $C_4$ raffinate-2 in place of 1-butene. $C_4$ raffinate-2 contained 78% of 1-butene and 2-butene (cis and trans), 18% of n-butane and isobutane, 1% of isobutene, 2% of 1,2- and 1,3-butadienes and a slight amount of minor constituents. In this case, the amount of carbonaceous substances accumulated on the catalyst to be returned to the reactor from the regenerator was 4.5% by mass. The above-mentioned reaction was continued for about 10 hours. A part of the reaction results obtained for 1 hour at any period during the reaction is shown in Table 1. The reaction results were substantially constant during the reaction.

Example 9

The Case Where a Starting Material Contained TBA and MTBE

Fluidized bed reaction was carried out by the catalyst recycling system under substantially the same conditions as in Example 1 except for feeding tert-butyl alcohol (TBA) and methyl tert-butyl ether (MTBE) so that a starting material may have a composition of 1-butene/water vapor/$N_2$/TBA/MTBE=20/40/38/1/1 by volume. In this case, the amount of carbonaceous substances accumulated on the catalyst to be returned to the reactor from the regenerator was 3.4% by mass. The above-mentioned reaction was continued for about 10 hours. A part of the reaction results obtained for 1 hour at any period during the reaction is shown in Table 1. The reaction results were substantially constant during the reaction.

Example 10

The Case Where Catalyst E Comprising Oxides of Mo and Cr was used

Fluidized bed reaction was carried out by the catalyst recycling system under substantially the same conditions as in Example 1 except for using catalyst E. In this case, the amount of carbonaceous substances accumulated on the catalyst to be returned to the reactor from the regenerator was 3.3% by mass. The above-mentioned reaction was continued for about 10 hours. A part of the reaction results obtained for 1 hour at any period during the reaction is shown in Table 1. The reaction results were substantially constant during the reaction.

Example 11

The Case Where Catalyst F Comprising Oxides of Mo and Ti was used

Fluidized bed reaction was carried out by the catalyst recycling system under substantially the same conditions as in Example 1 except for using catalyst F. In this case, the amount of carbonaceous substances accumulated on the catalyst to be returned to the reactor from the regenerator was 3.7% by mass. The above-mentioned reaction was continued for about 10 hours. A part of the reaction results obtained for 1 hour at any period during the reaction is shown in Table 1. The reaction results were substantially constant during the reaction.

Example 12

The Case Where Catalyst G Comprising Only Sn Oxide was used

Fluidized bed reaction was carried out by the catalyst recycling system under substantially the same conditions as in Example 1 except for using catalyst G. In this case, the amount of carbonaceous substances accumulated on the catalyst to be returned to the reactor from the regenerator was 1.0% by mass. The above-mentioned reaction was continued for about 10 hours. A part of the reaction results obtained for 1 hour at any period during the reaction is shown in Table 1. The reaction results were substantially constant during the reaction.

Example 13

The Case of using a Catalyst in which a Carrier was Silica-alumina

Fluidized bed reaction was carried out by the catalyst recycling system under substantially the same conditions as in Example 1 except for using catalyst H. In this case, the amount of carbonaceous substances accumulated on the catalyst to be returned to the reactor from the regenerator was 4.2% by mass. The above-mentioned reaction was continued for about 10 hours. A part of the reaction results obtained for 1 hour at any period during the reaction is shown in Table 1. The reaction results were substantially constant during the reaction.

When silica-alumina was used as the carrier, $CO_2$ in the reaction gas was extremely decreased.

Example 14

The Case Where Carbonaceous Substances were Accumulated by Pretreatment of a Catalyst A pretreater was provided between the regenerator and the reactor, and reaction was carried out in substantially the same manner as in Example 1. By adjusting the regeneration temperature to 600° C., the amount of carbonaceous substances accumulated on the catalyst to be introduced into the pretreater from the regenerator was adjusted to such an amount that carbonaceous substances had been substantially completely removed as in Comparative Example 1. In the pretreater, the catalyst was brought into contact with a gas consisting of 30% by volume of benzene, 20% by volume of 1,2- and 1,3-butadienes and 50 by volume of $N_2$ at 350° C. to accumulate carbonaceous substances on the catalyst. The amount of carbonaceous substances accumulated on the catalyst to be returned to the reactor from the pretreater was 2.0% by mass. The above-mentioned reaction was continued for about 10 hours. A part of the reaction results obtained for 1 hour at any period during the reaction is shown in Table 1. The reaction results were substantially constant during the reaction.

In addition, also when the same reaction as in Example 1 was carried out by the use of catalyst A except for using propylene and cyclohoxene in place of 1-butene as starting alkene, the catalyst on which the amount of carbonaceous substances accumulated thereon had been controlled at 0.1 to 10% by mass was effective in suppressing the production of fresh carbonaceous substances to improve the selectivity of acetone and cyclohexanone.

TABLE 1

| | Catalyst | Composition of catalyst Mo/(Sn + Mo) (atomic ratio) | Amount of carbonaceous substances on catalyst to be returned to reactor (mass %) | Amount of catalyst recycled/alkene (mass ratio) | $O_2$/alkene (volume ratio) | Water vapor/alkene (volume ratio) |
|---|---|---|---|---|---|---|
| Example 1 | A | 0.13 | 3.5 | 15 | 0.0 | 2.0 |
| Comparative Example 1 | A | 0.13 | 0.03 | 15 | 0.0 | 2.0 |
| Example 2 | A | 0.13 | 3.3 | 15 | 0.0 | 2.0 |
| Example 3 | A | 0.13 | 3.1 | 15 | 0.0 | 1.0 |
| Example 4 | B | 0.19 | 3.7 | 60 | 0.0 | 2.0 |
| Example 5 | B | 0.19 | 0.5 | 15 | 0.0 | 2.5 |
| Example 6 | C | 0.07 | 2.5 | 0.5 | 0.2 | 2.0 |
| Example 7 | A | 0.13 | 3.5 | 15 | 0.0 | 2.0 |
| Example 8 | A | 0.13 | 4.5 | 15 | 0.0 | 2.0 |
| Example 9 | A | 0.13 | 3.4 | 15 | 0.0 | 2.0 |

| | Regeneration temperature (° C.) | Amount of MEK produced (mmol) | Selectivity of MEK (%) | Selectivity of by-products (%) | Selectivity of carbonaceous substances (%) | Selectivity[*1] of MEK (%) |
|---|---|---|---|---|---|---|
| Example 1 | 320 | 632 | 86 | 4 | 10 | 95.6 |
| Comparative Example 1 | 600 | 624 | 50 | 4 | 46 | 92.6 |
| Example 2 | 320 | 520 | 90 | 4 | 6 | 95.7 |

TABLE 1-continued

| Example 3 | 320 | 648 | 91 | 3 | 6 | 96.8 |
| Example 4 | 280 | 616 | 85 | 5 | 10 | 94.4 |
| Example 5 | 500 | 376 | 70 | 5 | 25 | 93.3 |
| Example 6 | 280 | 500 | 86 | 10 | 4 | 89.6 |
| Example 7 | 320 | 640 | 86 | 4 | 10 | 95.6 |
| Example 8 | 320 | 610 | 87 | 5 | 8 | 94.6 |
| Example 9 | 320 | 628 | 86 | 5 | 9 | 94.5 |

| | Catalyst | Composition of catalyst Mo/(X + Mo) (atomic ratio) | Amount of carbonaceous substances on catalyst to be returned to reactor (mass %) | Amount of catalyst recycled/alkene (mass ratio) | $O_2$/alkene (volume ratio) | Water vapor/alkene (volume ratio) |
|---|---|---|---|---|---|---|
| Example 10 | E | 0.18*² | 3.3 | 15 | 0.0 | 2.0 |
| Example 11 | F | 0.18*² | 3.7 | 15 | 0.0 | 2.0 |
| Example 12 | G | Containing no Mo | 1.0 | 15 | 0.0 | 2.0 |
| Example 13 | H | 0.13 | 4.2 | 15 | 0.0 | 2.0 |
| Example 14 | A | 0.13 | 2.0 | 15 | 0.0 | 2.0 |

| | Regeneration temperature (° C.) | Amount of MEK produced (mmol) | Selectivity of MEK (%) | Selectivity of by-products (%) | Selectivity of carbonaceous substances (%) | Selectivity*¹ of MEK (%) |
|---|---|---|---|---|---|---|
| Example 10 | 320 | 356 | 80 | 8 | 12 | 90.9 |
| Example 11 | 320 | 636*³ | 88*³ | 6 | 10 | 93.6*³ |
| Example 12 | 320 | 52 | 60 | 25 | 15 | 70.6 |
| Example 13 | 320 | 424 | 82 | 8 | 10 | 91.1 |
| Example 14 | 320 | 432 | 75 | 6 | 19 | 92.6 |

*¹selectivity of MEK/(selectivity of MEK + selectivity of by-products) × 100: indicating the selectivity of MEK in the case of excluding carbonaceous substances produced (the purity of MEK).
*²Mo/(Cr + Mo) in Example 10 and Mo/(Ti + Mo) in Example 11.
*³The sum of MEK and butanol is shown only in Example 11. That is, the amount of MEK produced is the sum of 305 mmol of MEK and 331 mmol of butanol.

INDUSTRIAL APPLICABILITY

When an alcohol and/or a ketone are produced from a corresponding alkene(s) in a gas phase by the use of an oxide catalyst, the production method of the present invention has an inhibitory effect on the accumulation of carbonaceous substances on the catalyst during the reaction and hence permits great improvement of the selectivity of the desired product(s). Therefore, it becomes possible to limit loss of the starting alkene(s) caused by the production of carbonaceous substances and reduce utility cost necessary for the regeneration of the catalyst, and the like. Thus, said method is provided as a production method of the above-mentioned desired product(s) which has a very high productivity.

The invention claimed is:

1. A method for producing an alcohol and/or a ketone from at least one corresponding alkene by bringing a starting material containing the alkene(s), as a gas phase into contact with an oxide catalyst in the presence of water vapor to carry out the reaction, wherein
said method comprises taking out the oxide catalyst used in the reaction from a reactor, regenerating said oxide catalyst in the presence of an oxygen-containing gas, and returning the regenerated oxide catalyst to the reactor; and
said oxide catalyst satisfies the following requirements:
(a) it comprises an oxide(s) of molybdenum and/or tin, and
(b) the amount of carbonaceous substances accumulated on said oxide catalyst returned to the reactor is controlled to be within a range of 0.1 to 10% by mass.

2. A method according to claim 1, which comprises recovering the unreacted alkene(s) and the alcohol and/or ketone from a reaction mixture obtained by said reaction, and recycling the unreacted alkene(s) as a portion of the starting material.

3. A method according to claim 1 or 2, wherein said reaction is carried by a fluidized bed reaction system.

4. A method according to claim 3, wherein the temperature at the regeneration of the oxide catalyst in the presence of the oxygen-containing gas is 270 to 550° C.

5. A method according to claim 3, wherein the mass ratio of the amount of the oxide catalyst returned to the reactor to the amount of the alkene(s) fed to the reactor ranges from 0.5 to 100.

6. A method according to claim 1 or 2, wherein the amount of carbonaceous substances accumulated on the oxide catalyst is controlled to be within a range of 0.3 to 5% by mass.

7. A method according to claim 1 or 2, wherein the atomic ratio X of molybdenum to the sum of tin and molybdenum in the oxide catalyst {Mo/(Sn+Mo); wherein Mo is the number of atoms of molybdenum in said oxide catalyst, and Sn is the number of atoms of tin in said oxide catalyst} is in a range of $0 \leq X < 0.29$ or $0.29 < X < 0.51$ or $0.51 < X \leq 1$.

8. A method according to claim 1 or 2, wherein the atomic ratio X of molybdenum to the sum of tin and molybdenum in the oxide catalyst {Mo/(Sn+Mo); wherein Mo is the number of atoms of molybdenum in said oxide catalyst, and Sn is the number of atoms of tin in said oxide catalyst} is in a range of $0 \leq X < 0.29$ or $0.29 < X \leq 0.50$.

9. A method according to claim 1 or 2, wherein the atomic ratio X of molybdenum to the sum of tin and molybdenum in the oxide catalyst {Mo/(Sn+Mo); wherein Mo is the number of atoms of molybdenum in said oxide catalyst, and Sn is the number of atoms of tin in said oxide catalyst} is in a range of $0.01 \leq x \leq 0.24$.

10. A method according to claim 1 or 2, wherein the molar ratio of the amount of oxygen gas fed to the reactor to the amount of the alkene(s) fed to the reactor ranges from 0.0 to 0.5.

11. A method according to claim 1 or 2, wherein the molar ratio of the amount of water vapor fed to the reactor to the amount of the alkene(s) fed to the reactor ranges from 0.05 to 10.0.

12. A method according to claim 1 or 2, wherein the whole or a portion of recovered water after said reaction is reused in said reaction.

13. A method according to claim 1 or 2, wherein the alkene(s) is 1-butene and/or 2-butene.

14. A method according to claim 13, wherein the starting material containing 1-butene and/or 2-butene as the alkene(s) contains at least one compound selected from the group consisting of isobutene, butadiene, tert-butyl alcohol and methyl tert-butyl ether.

* * * * *

UNITED STATES PATENT AND TRADEMARK OFFICE
CERTIFICATE OF CORRECTION

| | |
|---|---|
| PATENT NO. | : 7,291,755 B2 |
| APPLICATION NO. | : 10/541367 |
| DATED | : November 6, 2007 |
| INVENTOR(S) | : Takashi Tsunoda et al. |

Page 1 of 1

It is certified that error appears in the above-identified patent and that said Letters Patent is hereby corrected as shown below:

On the title page, item (73), "Asahi Kasei Chemicals Corporation" should read --Maruzen Petrochemical Co., Ltd.--.

Signed and Sealed this
Tenth Day of March, 2015

Michelle K. Lee
*Deputy Director of the United States Patent and Trademark Office*